United States Patent [19]
Wipfelder et al.

[11] Patent Number: 5,883,214
[45] Date of Patent: *Mar. 16, 1999

[54] PROCESS FOR THE PREPARATION OF EPOXYSILANES

[75] Inventors: Ernst Wipfelder, München; Klaus Höhn, Taufkirchen, both of Germany

[73] Assignee: Siemens Aktiengesellschaft, Munich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 602,847
[22] PCT Filed: Aug. 16, 1994
[86] PCT No.: PCT/DE94/00934
  § 371 Date: Feb. 23, 1996
  § 102(e) Date: Feb. 23, 1996
[87] PCT Pub. No.: WO95/06050
  PCT Pub. Date: Mar. 2, 1995

[30] Foreign Application Priority Data

Aug. 24, 1993 [DE] Germany ................ 43 28 465.5

[51] Int. Cl.$^6$ ..................................... C08G 77/08
[52] U.S. Cl. ................ 528/17; 528/18; 549/215
[58] Field of Search ............... 549/215; 528/18, 528/17

[56] References Cited

U.S. PATENT DOCUMENTS

| | | | |
|---|---|---|---|
| 3,455,877 | 7/1969 | Plueddemann et al. | 260/46.5 |
| 3,563,941 | 2/1971 | Plueddemann et al. | 260/28 |
| 3,647,846 | 3/1972 | Hartlein et al. | 260/448.2 E |
| 4,902,739 | 2/1990 | Ona et al. | 549/215 |
| 5,109,094 | 4/1992 | Rees et al. | 524/14 |
| 5,292,849 | 3/1994 | Fujioka et al. | 528/18 |
| 5,300,608 | 4/1994 | Chu et al. | 528/14 |

OTHER PUBLICATIONS

White, et al., "Organofunctional Siloxanes", Chapter 4, p. 193–210, *Siloxane Polymers,* Simon & Schuster Co., Englewood Cliffs, NJ, 1993.

Wipfelder, et al., "Epoxysiloxane Resins by the Condensation of 3–Glycidloxypropyltrimethyoxysilane with Diphenylsilanediol", *Die Angewandte Makromolekulare Chemie* 218, pp. 111–126, 1994.

Rüdiger Nass, et al., J. Non–Cryst. Solids, 121, 370–374 (1990).

G. Philipp et al., J. Non–Cryst. Solids, 82, 31–36 (1986).

*Primary Examiner*—Margaret Glass
*Attorney, Agent, or Firm*—Hill & Simpson

[57] ABSTRACT

Epoxysilanes having epoxide groups bonded via SiC are obtained by reaction of epoxyalkoxysilanes with silanols. The transparent siloxane mixtures containing epoxide can be employed directly as resin components for mixing with epoxy resins for casting resin applications.

8 Claims, No Drawings

PROCESS FOR THE PREPARATION OF EPOXYSILANES

BACKGROUND OF THE INVENTION

Silicones and siloxanes can be employed for flexibilizing reactive resins. To obtain a chemically stable molded material, those siloxanes which participate in the curing reaction of the reactive resin and are incorporated chemically into the molded material are preferred.

Siloxanes which contain epoxide groups and can be bonded into a molded material in a stable and hydrolysis-resistant manner with the epoxide group via SiC bonds are therefore sought for mixing with epoxy resins.

Epoxysilanes having epoxide groups bonded via SiC are obtained by hydrosilylation of silane hydrides with unsaturated epoxide compounds. Under technologically demanding conditions, with exclusion of water and in an absolute inert gas atmosphere, reaction products can be obtained which must be worked up in expensive purification steps and must be freed from the platinum metal group catalyst required.

Epoxysilanes can also be rendered accessible by epoxidation of unsaturated silane compounds. This is also an involved synthesis which leads to expensive products.

The object of the present invention is therefore to provide a simple process for the preparation of epoxysilanes having epoxide groups bonded via SiC, which leads to a product which is stable to chemicals and heat, has an adequate epoxide content, is compatible with the usual epoxy resins for casting resin applications and can be cured together with these. SUMMARY OF THE INVENTION

SUMMARY OF THE INVENTION

This object is achieved according to the invention by a process having the features of claim 1. Further embodiment of the invention and a preferred use for the process product are to be found in the other claims.

The process accordinig to the invention can be carried out in a simple one-pot reaction in a short time under normal condition with respect to atmosphere and pressure with minimum expenditure on the process. A mixture of various siloxanes which comprises chiefly cyclic tri- and tetrameric condensation products is obtained as the product. If the reaction conditions remain constant, the process can be carried out reproducibly. Transparent oils which result in transparent molded materials when mixed with corresponding resin components can be obtained in the process. The product is compatible with the usual epoxy resins and can be mixed with them in all proportions as a further resin component without further purification or working up. The epoxide value of the resulting siloxanes, predetermined by the nature and the ratio of the amounts of the starting substances, results in a product which is readily capable of crosslinking. This can be stored for several months with only a slight increase in viscosity and only a slight reduction in the epoxide value. It has a high stability to heat and thermal oxidation, which is also retained in the molded material obtained after curing of a corresponding mixture with the usual epoxy resins.

During the condensation reaction, an Si—O—Si bond is formed from the alkoxy group of the epoxysilane and the OH group of the silanol, the corresponding alkyl alcohol being split off. Various homocondensation products of the silanol are observed as a side reaction. However, the predominant fraction of the siloxane mixture obtained as the product comprises the trimeric and tetrameric condensation products mentioned containing epoxide groups, in which the ratio of cyclic to linear products can be adjusted according to the reaction procedure and is, for example, 2:1. By-products which are obtained by reaction of the epoxide groups with the starting substances, intermediates or end products are also obtained to a small extent.

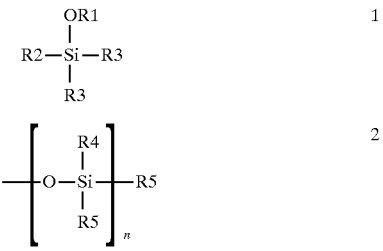

The epoxyalkoxysilane 1 employed as the starting compound carries 1 to 3 alkoxy groups which are capable of condensation. The radical R1 can be chosen as desired, but is preferably an alkyl radical having 1 to 6 C atoms, since the reactivity of the group to be split off during the condensation decreases as the chain length of the alkyl radical increases. The most reactive starting compounds are thus the epoxymethoxysilanes. Ethyl can also be preferred as the alkyl group because of the acceptability of the ethyl alcohol split off.

Monomeric epoxyalkoxysilanes 1 are preferred because of easier availability, but the reaction is in principle also possible with corresponding longer-chain alkoxysiloxanes.

Correspondingly longer-chain silanols 2 which contain OH groups as reactive groups in the α-position, α- and ω-position or in the chain are more easily available and inexpensive. The choice of the other organic group R4 bonded via SiC is not critical and this can be any desired alkyl or aryl radical. The index n, which defines the number of siloxane units, can be freely chosen between 1 and 12. Depending on the other radicals, however, an increasing incompatibility of the condensation products with epoxy resins may result as the chain length increases, which can render their later desired use as a resin component as d mixture with precisely these epoxy resins difficult or impossible.

The radical R2, containing epoxide groups, of the starting compound 1 is bonded to silicon via a C atom and can otherwise be chosen freely. Depending on the availability of the corresponding epoxyalkoxysilane, R2 can be a glycidyloxyalkyl, an epoxyalkyl, an epoxyaryl or an epoxycycloalkyl group. The corresponding glycidyl compounds which are obtained by reaction of correspondingly reactive compounds with epichlorohydrin are readily available.

A condensation catalyst may be necessary to assist the reaction, depending on the reactivity of the starting substances, which may be electronically and sterically hindered. There are no restrictions on the catalyst in respect of the reaction itself, so that any desired condensation catalyst is suitable. Taking into account the preferred or intended use of the product as a resin component for reactive resins, however, the catalyst is chosen such that the epoxide group is retained as far as possible during the condensation. A catalyst which is ideal in this respect therefore is neither decidedly basic nor decidedly acid, and in the ideal case is neutral.

The reaction of the starting substances can be carried out in solution in suitable solvents, for example in alcohols, ethers or the like. It is also possible to carry out the reaction as a bulk reaction without a solvent. To obtain exclusively clear and transparent products, the reaction is catalyzed and is carried out as a bulk reaction.

The reaction can take place in an open reaction vessel and is carried out with an increase in temperature. Preferred reaction temperatures are between 80° and 150° C. Volatile reaction products are preferably driven off during the reaction, for example by blowing an inert gas (for example nitrogen) into the reaction mixture. This increases the storage life and stability of the product itself and of its mixture with reactive resins.

The composition of the product depends on the reaction conditions, in particular on the stoichiometry of the batch, the reaction temperature and not least the duration of the reaction, which may also substantially influence the composition of the product. A stoichiometric batch of the starting substances is composed such that one OH group in the silanol 2 is available per alkoxy group which can be split off in the epoxysilane 1. Because of the homocondensation observed to a small extent, products containing alkoxy groups can also be detected in the case of a stoichiometric batch. In contrast, the silanol 2 is reacted completely. The product is a usually colorless transparent oil which can be mixed with the usual reactive resins in any mixing ratio. Novel reactive resin mixtures which are stable to storage for several months can be obtained with aliphatic and aromatic glycidyl ethers, in particular those based on bisphenol A and F, with corresponding glycidyl esters, aliphatic and cycloaliphatic epoxides and any other desired epoxides, for example those obtained by epoxidation of unsaturated compounds. The storage stability of the reactive resin mixture with the novel epoxysiloxane can be increased further by heating the reactive resin mixtures under a vacuum.

In the corresponding reactive resin mixtures, the epoxysiloxanes, which are also compatible with the curing process for the reactive resin, give transparent molded materials, the glass transition temperature of which is unusually high compared with other siloxane-containing molded materials. Expressed more clearly, an only slight reduction in the glass transition temperature of the molded material compared with that of the pure epoxy resin is observed with the siloxane-containing reactive resin mixture. Moreover, the thermal and thermally oxidative properties of said epoxy resin are retained.

The siloxane condensates according to the invention containing epoxide groups in general show an improved compatibility with the constituents of epoxide formulations compared with epoxysiloxanes prepared conventionally. The chemistry (reactivity) of the epoxy resin formulations is not impaired by admixing the epoxysiloxanes according to the invention. All components are soluble in one another and give low-viscosity resins for casting resin applications. Compared with epoxysiloxanes which are obtained by hydrosilylation, the further advantage of a highly simplified and inexpensive preparation, and in particular of the ability of the product to be used directly as a resin component without prior purification, results. Hydrosilylated epoxysiloxanes furthermore are neither clear nor transparent or stable in color.

DETAILED DESCRIPTION OF THE INVENTION

The invention is described in more detail below with the aid of an embodiment example.

EMBODIMENT EXAMPLE:

3-Glycidyloxypropyltrimethoxysilane (GPT) which is already known as an adhesion promoter for epoxy resins and has already been admixed to customary epoxy resins in amounts of about 0.25 percent is used as the alkoxysilane 1. Diphenylsilanediol (DPS) is chosen as the silanol 2.

0.13 mol of GPT is mixed with in each case 1 percent by weight of isopropyl titanate (IPT) or dibutyltin dilaurate, and 0.2 mol of DPS is added in portions at 120° C. (or at 80° C.) in the course of 15 minutes. The DPS dissolves with evolution of methanol. The reaction mixture is heated under reflux for six hours and then at 120° C. under 3 mmHg for two hours.

Volatile reaction products are driven off with a stream of nitrogen.

Transparent oils are obtained, the average molecular mass weight of which, determined by vapor pressure osmometry, is 1550 g/mol (CHCl$_3$).

With the solvent-free reaction, starting substances are no longer detected in the product. This contains small amounts of cyclo-hexaphenyltrisiloxane and cyclo-octaphenyltetrasiloxane, which are formed by homocondensation of DPS.

The product obtained with IPT as the catalyst remains transparent during storage and heating to 150° C. The epoxide value, determined by titration, shows that most of the epoxide groups are retained during the reaction. It is found from the $^1$H-NMR spectrum of the product mixture that about one SiOCH$_3$ unit is retained in the product per GPT employed. This means that on average only two of the total of three methoxy functions of GPT are reacted.

HPLC analyses give four groups of signals, which can be assigned to linear trimers, linear tetramers, cyclic trimers and cyclic tetramers. In the solvent-free batch at 120° C. with IPT as the catalyst, these components are found in a concentration of, for example, 13:20:28:39. The cyclic siloxanes consist of 3-glycidyloxypropylmethoxysilane and diphenylsilane fragments as condensation units which originate from GPT and TPS.

The thermal properties of this product mixture were investigated in TG/DTA experiments. Thermal degradation takes place in two exothermic stages at 401° C. and 555°C. In the first stage, a weight loss of about 40 percent is observed up to 500° C. and of a further 15 percent up to 750° C. The siloxane structures and the diphenylsilane units are responsible for the high pyrolysis residue of 45.2 percent at 750° C. After combustion of the carbon black content in air, a residue of 23.9% results at 800° C. The stepwise degradation and high pyrolysis and combustion residue indicate favorable thermal properties of the product. Some properties of the epoxysilane product are summarized in the following table.

TABLE

| | |
|---|---|
| Synthesis | Reproducible |
| Color | Pale yellow, transparent |
| Refractive index $n_D^{20}$ | 1.565 |
| Viscosity in mPas | |
| at 25° C. | 62,000 to 66,000 |
| at 60° C. | 1800 to 2000 |
| Epoxide value (mol/100 g) | |
| found | 0.175 to 0.180 |
| calculated | 0.215 |
| Compatibility | Good with organic epoxides |
| Storage stability at room temperature | Epoxide value EEW decreases by 9 percent in 30 days |

Resins which are stable to storage and are suitable for casting resin applications in electronics are also obtained in mixtures with known epoxy resin formulations. The molded materials produced in this way have good thermomechanical stress properties and can be produced in transparent form. The temperature-dependence of the modulus of elasticity is low.

We claim:

1. A method for making epoxyalkoxy functional siloxane trimers and tetramers having Si-C bonded epoxide groups, comprising the steps of:

reacting approximately stoichiometric amounts of an epoxyalkoxysilane of the formula:

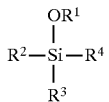

wherein $R^1$ is selected from alkyl radicals having 1 to 6 carbon atoms and aryl radicals, R2 is selected from glycidyloxyalkyl, epoxyalkyl and epoxycycloalkyl radicals, and $R^3$ and $R^4$ are independently selected from alkyl radicals, aryl radicals, $OR^1$ and $R^2$;

with a silanol of the formula:

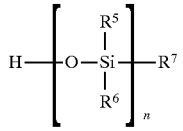

wherein $R^5$ is selected from alkyl radicals and aryl radicals, $R^6$ and $R^7$ are independently selected from OH and $R^5$, and n is an integer greater than or equal to 1 and less than or equal to 12: under condensation reaction conditions at a temperature of from about 80° to about 150° C. a pH of from about 5 to about 8 in the presence of a neutral condensation catalyst selected from the group consisting of isopropyl titanate and dibutyl tin dilaurate, until formation of an epoxyalkoxy functional siloxane trimer or tetramer is obtained.

2. A method as defined in claim 1, wherein the epoxyalkoxy functional siloxane trimers and tetramers are comprised of cyclic trimers and cyclic tetramers.

3. A method as defined in claim 1, wherein the epoxyalkoxy functional siloxane trimers and tetramers comprise a mixture of linear trimers, linear tetramers, cyclic trimers and cyclic tetramers wherein the ratio of cyclic trimers and tetramers to linear trimers and tetramers is about 2:1.

4. A method as defined in claim 1, in which the reaction is carried out as a bulk reaction.

5. A method as defined in claim 1, wherein substantially stoichiometric amounts of epoxyalkoxysilane and silanol are reacted.

6. A method as defined in claim 1, wherein said reaction is conducted under a flow of an inert gas and any volatile reaction products produced are removed in the flow of inert gas.

7. A method as defined in claim 1, further comprising the step of isolating condensation reaction products after reaction times of from about 2 to about 24 hours.

8. A method as defined in claim 1, further comprising the step of heating the epoxy-functional siloxane reaction product under vacuum conditions to provide improved storage stability.

* * * * *